(12) United States Patent
Dahnke et al.

(10) Patent No.: US 8,175,678 B2
(45) Date of Patent: May 8, 2012

(54) MULTIPLE CONTRAST AGENT INJECTION FOR IMAGING

(75) Inventors: Hannes Dahnke, Hamburg (DE); Tobias Schaeffter, Blackheath (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 1091 days.

(21) Appl. No.: 12/066,510

(22) PCT Filed: Sep. 7, 2006

(86) PCT No.: PCT/IB2006/053143
§ 371 (c)(1),
(2), (4) Date: Mar. 12, 2008

(87) PCT Pub. No.: WO2007/031910
PCT Pub. Date: Mar. 22, 2007

(65) Prior Publication Data
US 2009/0130023 A1 May 21, 2009

(30) Foreign Application Priority Data
Sep. 13, 2005 (EP) .................... 05108409

(51) Int. Cl.
*A61B 5/055* (2006.01)
(52) U.S. Cl. .......................... 600/420
(58) Field of Classification Search ............. 600/410, 600/420
See application file for complete search history.

(56) References Cited

U.S. PATENT DOCUMENTS

| | | | |
|---|---|---|---|
| 5,164,297 A | 11/1992 | Josephson et al. | |
| 5,789,921 A * | 8/1998 | Albert et al. | 324/300 |
| 7,567,832 B2 * | 7/2009 | Schmainda et al. | 600/410 |
| 2002/0026116 A1 | 2/2002 | Schmainda | |
| 2003/0125617 A1 | 7/2003 | Bjornerud et al. | |
| 2004/0073117 A1 * | 4/2004 | Schwarz et al. | 600/458 |
| 2004/0254523 A1 | 12/2004 | Fitzgerald et al. | |
| 2008/0305049 A1 * | 12/2008 | Degani et al. | 424/9.363 |

FOREIGN PATENT DOCUMENTS

| | | |
|---|---|---|
| WO | WO0057777 A1 | 10/2000 |
| WO | WO03007010 A1 | 1/2003 |

OTHER PUBLICATIONS

Tofts et al: "Quantitative Analysis of Dynamic GD-DTPA Enhancement in Breast Tumors Using a Permeability Model"; Magnetic Resonance in Medicine, Academic Press, vol. 33, No. 4, April 1995, pp. 564-568.

Bjornerud et al: "Assessment of T1 and T2 Effects in Vivo and EX Vivo Using Iron Oxide Nanoparticles in Steady State-Dependence on Blood Volume and Water Exchange"; Magnetic Resonance in Medicine, vol. 47, pp. 461-471, 2002.

Bremer et al: "Steady-State Blood Volume Measurements in Experimental Tumors With Differenet Angiogenic Burdens—A Study in MICE"; Radiology, vol. 226, pp. 214-220, Jan. 2003.

* cited by examiner

*Primary Examiner* — Jacqueline Cheng

(57) ABSTRACT

MRI based molecular imaging is strongly supported by the accurate quantification of contrast agents. According to an exemplary embodiment of the present invention, contrast agent is applied on the basis of a multiple injection application scheme, during which changes in relaxation rate are determined. This may provide for an accurate determination of tumor vascularity via MRI relaxometry.

14 Claims, 3 Drawing Sheets

MULTIPLE CONTRAST AGENT INJECTION FOR IMAGING

The present invention relates to the field of imaging. In particular, the present invention relates to an examination apparatus for examination of an object of interest, to an image processing device, to a computer-readable medium, to a program element and to a method of examination of an object of interest.

Magnetic resonance based molecular imaging (MRI) is strongly supported by an accurate quantification of contrast agents. The monitoring of therapy effects like changing tumor vascularization and perfusion are of great importance in the clinical routine. Detecting therapy effects requires an accurate and quantitative determination of contrast agent concentrations that induce changes in MR relaxation rates $R_1$, $R_2$ and $R_2^*$.

By using a method for quantitatively measuring these changes in the relaxation rates $\Delta R_2^*$ before and after contrast agent application, the contrast agent induced change in relaxation rate may be quantified.

However, the accuracy of the examination result is limited by the accuracy of the quantification of the tumor vascularity.

It may be desirable to have an improved quantification of a vascularity of an object of interest.

According to an exemplary embodiment of the present invention, an examination apparatus for examination of an object of interest may be provided, the examination apparatus comprising an acquisition unit adapted for measuring a first contrast agent concentration after a first contrast agent application and before a second contrast agent application and for measuring a second contrast agent concentration after the second contrast agent application, resulting in a series of measured contrast agent concentration values as a function of an overall contrast agent application value.

Thus, by providing a multiple injection scheme of contrast agent, which contrast agent is applied to the object of interest, each injection or application of the contrast agent may be added to an already present contrast agent amount in the object of interest, for example in the blood stream of a patient. The contrast agent concentrations are e.g. determined at different times (and therefore at a different overall contrast agent application value). This may provide for an improved quantification of a vascularity of, for example, a tumor.

According to another exemplary embodiment of the present invention, the examination apparatus further comprises a contrast agent application unit adapted for performing the first contrast agent application at a first predetermined time and for performing the second contrast agent application at a second predetermined time.

Therefore, according to this exemplary embodiment of the present invention, it may be predetermined, at which respective times each contrast agent application will be performed. For example, the time scale between consecutive applications may be much smaller than the typical time scale during which the contrast agent inside the object of interest becomes defective. Furthermore, according to this exemplary embodiment of the present invention, the time between different contrast agent applications may be varied. This may lead to a flexible examination procedure.

According to another exemplary embodiment of the present invention, the examination apparatus is a magnetic resonance examination apparatus, wherein the first contrast agent concentration is measured on the basis of a first relaxation rate and wherein the second contrast agent concentration is measured on the basis of a second relaxation rate, resulting in a series of measured relaxation rate values as a function of an overall contrast agent application value.

Therefore, relaxation rates (which relate to contrast agent concentrations) may be measured by the acquisition unit on the basis of an MRI measurement.

According to another exemplary embodiment of the present invention, the examination apparatus further comprises a determination unit adapted for determining a change in relaxation rate per injected amount of contrast agent on the basis of the series.

Therefore, for example, the determination unit may be adapted for performing a plurality of relaxation rate measurements at different times and therefore for different overall contrast agent application values on the basis of which changes in the relaxation rate may be calculated.

According to another exemplary embodiment of the present invention, the first relaxation rate is based on a spin-spin transverse relaxation rate and incorporates magnetic field inhomogeneities.

This may provide for a good relaxation rate determination, since this relaxation rate shows a high sensitivity for iron oxide based contrast agents.

According to another exemplary embodiment of the present invention, the series of measured contrast agent concentration values (or, in case of an MRI examination apparatus, relaxation rate values) as a function of the overall application value has a linear slope, wherein the determination unit is further adapted for fitting the linear slope. The fitting is performed on the basis of a weighting of the first measured contrast agent concentration (or first measured relaxation rate) with a corresponding first error bar and a weighting of the second measured contrast agent concentration (or first measured relaxation rate) with a corresponding second error bar.

Thus, according to this exemplary embodiment of the present invention, an average slope of the contrast agent concentration value—overall contrast agent application value curve may be determined. For example, the curve may be linearly fitted by taking into account possible errors of the measured values. This may result in an accurate slope determination.

It should be noted, however, that other fitting procedures may be performed.

According to another exemplary embodiment of the present invention, the determination unit is further adapted for monitoring deviations of a linearity of the slope and for determining a leakiness of the object of interest on the basis of the monitored deviations.

For example, in case the object of interest is a tumor, the leakiness of the vessels inside tumor may thus be assessed.

The determination of the leakiness may be performed on the basis of a fit of a non-linear model to the series of measured relaxation rate values. Therefore, since a leaky tumor may lead to an accumulation of contrast agent, the leaky tumor may therefore be distinguished from a non-leaky tumor by fitting the non-linear model to the $\Delta R_2^*$ versus contrast agent curve.

Such a non-linear model may, for example, be provided in form of a function that shows a quadratic slope or even a higher order slope, due to the accumulation of the contrast agent outside of the leaky vessel.

According to another exemplary embodiment of the present invention, the object of interest comprises a first voxel and a second voxel, wherein the monitoring of deviations of the linearity of the slope is performed for the first voxel and the second voxel, resulting in a discrimination of different areas within the object of interest.

Therefore, according to this exemplary embodiment of the present invention, by calculating the deviations from linearity for each voxel different areas within one tumor may be distinguished.

According to another exemplary embodiment of the present invention, the contrast agent application unit is further adapted for performing the first contrast agent application and the second contrast agent application during a continuous injection procedure.

For example, according to this exemplary embodiment of the present invention, the injection rate of contrast agent application may be constant during the application procedure. However, the injection rate may be varied during the application, for example by having a higher injection rate at the beginning of the application and having a lower injection rate at the end of the application.

According to another exemplary embodiment of the present invention, the contrast agent is a superparamagnetic iron-oxide contrast agent (SPIO).

According to another exemplary embodiment of the present invention, the contrast agent is a targeted contrast agent.

According to another exemplary embodiment of the present invention, the examination apparatus may be applied as a baggage inspection apparatus, a medical application apparatus, a material testing apparatus or a material science analysis apparatus. A field of application of the invention may be material science analysis, since the defined functionality of the invention may allow for a secure, reliable and highly accurate analysis of a material.

According to another exemplary embodiment of the present invention, the examination apparatus may be configured as one of the group consisting of a magnetic resonance examination apparatus (MR), a computed tomography examination apparatus (CT), a positron emission tomography apparatus (PET), a single photon emission computed tomography apparatus (SPECT), an x-ray imaging apparatus, and an ultrasound imaging apparatus.

According to another exemplary embodiment of the present invention, an image processing device for examination of an object of interest may be provided, the image processing device comprising a memory for storing a dataset of the object of interest. The dataset may comprise a first contrast agent concentration, measured after a first contrast agent application and before a second contrast agent application, and a second contrast agent concentration measured after the second contrast agent application, resulting in a series of measured contrast agent concentration values as a function of an overall contrast agent application value.

Therefore, an image processing device may be provided which is adapted for performing an improved quantification of a vascularity of an object of interest by processing a dataset comprising multiple relaxation rates being acquired during a multiple injection scheme of a contrast agent.

Furthermore, the image processing device may be adapted for determining a change in relaxation rate per injected amount of contrast agent on the basis of the series.

According to another exemplary embodiment of the present invention, a method of examination of an object of interest may be provided, the method comprising the steps of performing a first contrast agent application, performing a second contrast agent application and measuring a first contrast agent concentration after the first contrast agent application and before the second contrast agent application and measuring a second contrast agent concentration after the second contrast agent application, resulting in a series of measured contrast agent concentration values as a function of an overall contrast agent application value.

Thus, a method is provided for an examination of an object of interest which may lead to an improved quantification of a vascularity of an object of interest, such as a tumor.

According to another exemplary embodiment of the present invention, a computer-readable medium may be provided, in which a computer program of examination of an object of interest is stored, which, when being executed by a processor, is adapted to carry out the above-mentioned method steps.

Furthermore, the present invention relates to a program element of examination of an object of interest, which may be stored on the computer-readable medium. The program element may be adapted to carry out the steps of performing a first contrast agent application, performing a second contrast agent application, measuring a first contrast agent concentration and measuring a second contrast agent concentration, each of them being measured at a specific predetermined time during contrast agent application.

The program element may preferably be loaded into working memories of a data processor. The data processor may thus be equipped to carry out exemplary embodiments of the methods of the present invention. The computer program may be written in any suitable programming language, such as, for example, C++ and may be stored on a computer-readable medium, such as a CD-ROM. Also, the computer program may be available from a network, such as the WorldWideWeb, from which it may be downloaded into image processing units or processors, or any suitable computers.

It may be seen as the gist of an exemplary embodiment of the present invention, that the difference in the relaxation rate $\Delta R_2^*$ is measured with a multiple injection scheme of contrast agent. Since the blood cycle time is longer than the total measurement time, each injection is added to the already present contrast agent amount in the blood stream. This may lead to a series of $\Delta R_2^*$ values showing a linear rise of $\Delta R_2^*$ versus contrast agent concentration. This may provide for an improved determination of $\Delta R_2^*$ versus contrast agent concentration and may thus provide for an improved quantification of a vascularity of a tumor.

These and other aspects of the present invention will become apparent from and elucidated with reference to the embodiments described hereinafter.

Exemplary embodiments of the present invention will be described in the following, with reference to the following drawings.

The illustration in the drawings is schematically. In different drawings, similar or identical elements are provided with the same reference numerals.

Figure 1:
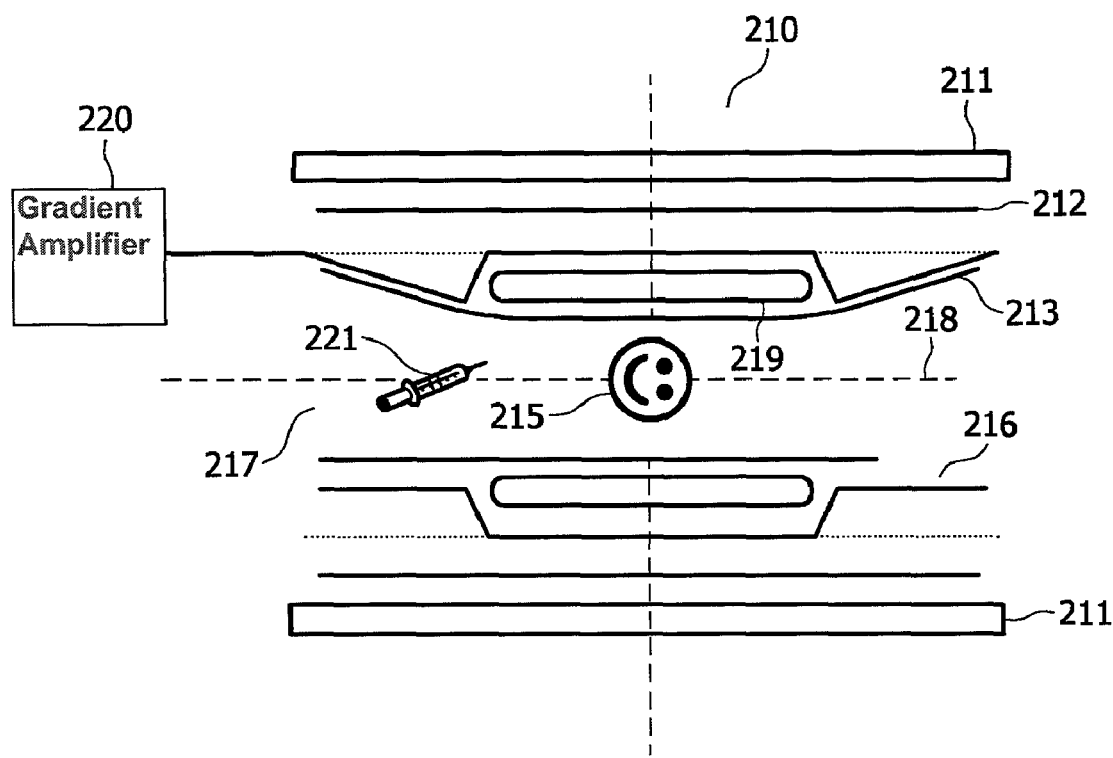
FIG. 1 shows a simplified schematic representation of an MRI apparatus according to an exemplary embodiment of the present invention.

FIG. 1 shows a simplified schematic representation of an embodiment of an MRI scanner system according to the present invention. The MRI scanner system comprises coils 210 which are arranged along an axis 218 and surround an examination space 217, in which a patient 215 or another object of interest, such as, for example, a material to be tested or examined, is positioned. However, it should be clear, that the described examination apparatus may be used in different fields, such as, for example, material science analysis.

Advantageously, the object of interest 215 lies on a movable table or conveyor belt 216, which is disposed at the lower part of the examination space 217. The system of coils 210 surrounding the examination space 217 comprises an HF-coil 219, actively shielded arrangement of gradient coils comprising an inner coil 213 and an actively shielded coil or shield 212 and a cryostat 211, in which the coils are arranged in order to be cooled down during generation of the magnetic field.

The arrangement of gradient coils 213, 212 may be connected to a gradient amplifier 220 and to a determination unit (not depicted in FIG. 1) adapted for determining a change in relaxation rate per injected amount of contrast agent on the basis of a series of measured relaxation rate values.

Furthermore, the MRI scanner system may comprise a motor control unit with respective motors (not depicted in FIG. 1), for example for moving the conveyor belt 216.

According to an aspect of the present invention, the MRI scanner system may further comprise a contrast agent application unit 221 which is adapted for the application of the contrast agent into the object of interest, for example at a constant rate during a predetermined time interval. Furthermore, the contrast agent application unit 221 may be adapted for performing different contrast agent application steps in the form of a multi-step injection scheme.

It should be noted, however, that the present invention is not limited to MR imaging, but may also be applied in the field of CT/CSCT imaging, in the field of PET imaging, in the field of SPECT imaging, in the field of x-ray imaging or in the field of ultrasound imaging.

Figure 2:
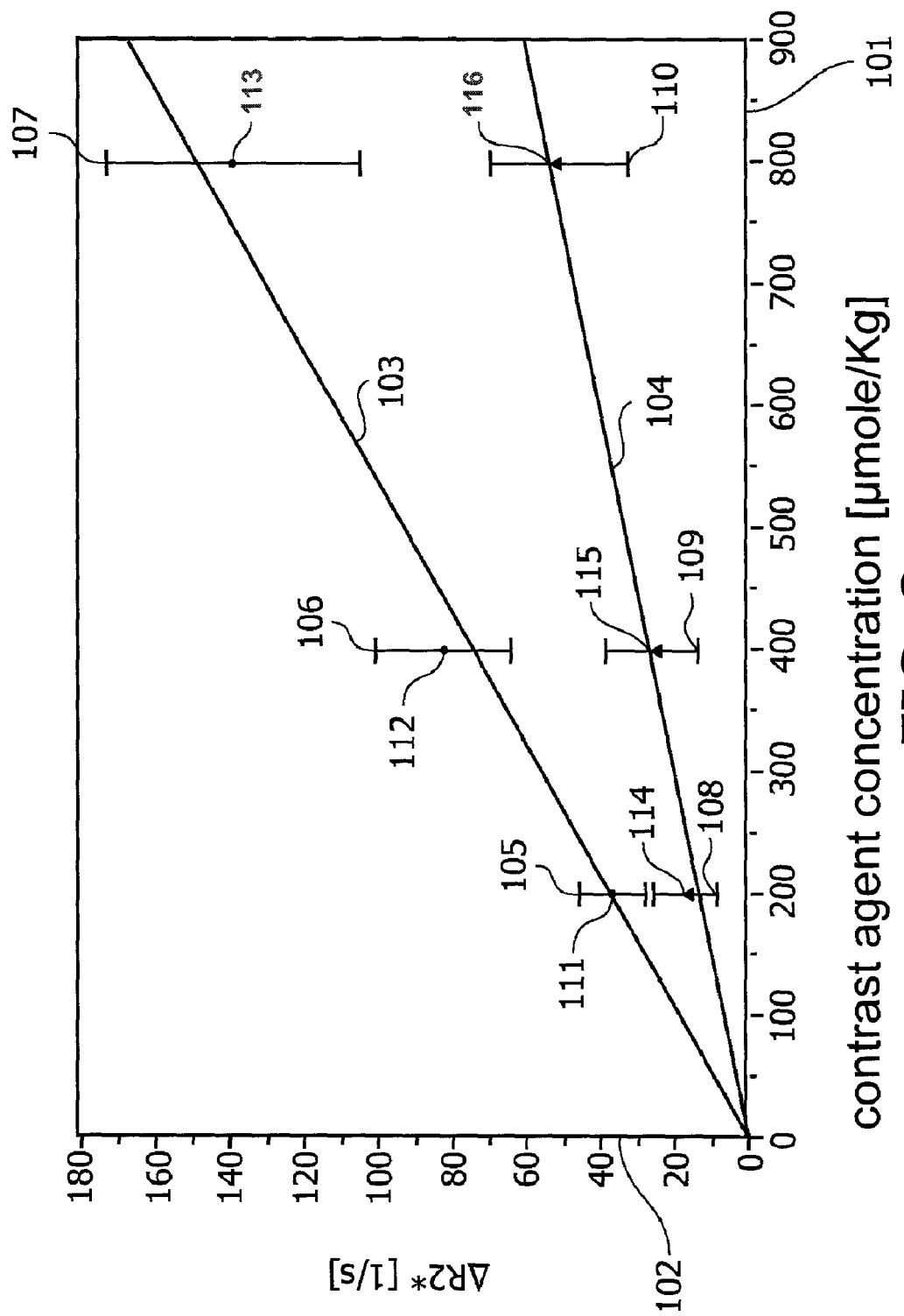
FIG. 2 shows a schematic representation of measured $\Delta R_2^*$ values at different overall contrast agent application values.

FIG. 2 shows a schematic representation of measured $\Delta R_2^*$ values at different overall contrast agent application values. The horizontal axis 101 shows the overall contrast agent application value (which is the contrast agent concentration in the blood stream of the patient) in units of $\mu mol/kg$, ranging from 0 $\mu mol/kg$ to 900 $\mu mol/kg$. The vertical axis 102 depicts the $\Delta R_2^*$ values of three injections of the contrast agent in units of $1/s$. The vertical axis 102 ranges from 0 to 180 $1/s$.

An example for a contrast agent applied or injected into the blood stream of a patient is Supravist, distributed by Schering AG. However, other contrast agents may be used.

The lower curve 104 shows results of a low vascularized mouse tumor and the upper curve 103 shows the results of a highly vascularized mouse tumor. The linear fits 103, 104 to the measured data points 111-113 and 114-116, respectively, may be performed by weighting the data points with their respective error bars 105 to 107 and 108 to 110.

In order to assess for example the vascularity of a tumor, the change in relaxation rate $\Delta R_2^*$ needs to be normalized to the injected amount of contrast agent for each voxel of the object of interest. For highly vascularized tumors a higher value of $\Delta R_2^*$ versus contrast agent concentration may be measured than for low vascularized tumors (as depicted in FIG. 2). A decrease of vascularity during therapy may therefore be monitored by measuring $\Delta R_2^*$ versus blood contrast agent concentration. This may be determined with one single injection of contrast agent assuming that before contrast agent injection the change $\Delta R_2^*$ is 0.

However, according to an aspect of the present invention, $\Delta R_2^*$ may be measured with a multiple injection scheme using the same total amount of contrast agent. Assuming a blood cycle time longer than the total measurement time, each injection may be added to the already present contrast agent amount in the blood stream. The injection scheme may be a multi-step scheme or a continuous injection over the measurement time, assuming that the measurement of one $\Delta R_2^*$ map is fast compared to the injection rate. Measuring $\Delta R_2^*$ after each injection may lead to a series of $\Delta R_2^*$ values, which may show a linear rise of $\Delta R_2^*$ versus contrast agent concentration. Fitting with linear slope may yield the change in relaxation rate per injected amount of contrast agent. This fit may be performed, for example, by weighting the data points with their respective error bars 105, 106, 107 and 108, 109, 110. Since several data points may be generated by using the same dose of contrast agent as for one single injection of the total amount, a more accurate value of $\Delta R_2^*$ versus contrast agent concentration may be calculated as shown in FIG. 2.

For example, by analyzing the last data points 113 (for curve 103) and 116 (for curve 104), the following slopes of the curve which are a measure for the tissue vascularity may be determined:

0.17±0.04 $kg/(s*\mu mol)$ for the high vascularization 103 and 0.0625+0.02 $kg/(s*\mu mol)$ for the low vascualarization 104.

By analyzing the weighted linear fit, the value for the high vascularization curve is 0.18+0.01 $kg/(s*\mu mol)$ and the value for the low vascularization 104 is 0.066+0.005 $kg/(s*\mu mol)$.

Therefore, the uncertainty is a factor of 4 lower in the multi-injection scheme without using a higher amount of contrast agent. This may result in an improved examination result.

According to another aspect of the present invention, additional information may be drawn from the multi-injection curve. By monitoring deviations of the linearity of the slope parameters like the leakiness of the tumor may be assessed. A leaky vessel network inside the tumor may lead to an accumulation of contrast agent and may therefore be distinguished from a non-leaky tumor by fitting a non-linear model to the $\Delta R_2$ versus contrast agent curve. Also, areas of restricted blood flow may be assessed by this method. By calculating these deviations from linearity for each voxel also different areas within one tumor may be distinguished.

Figure 3:
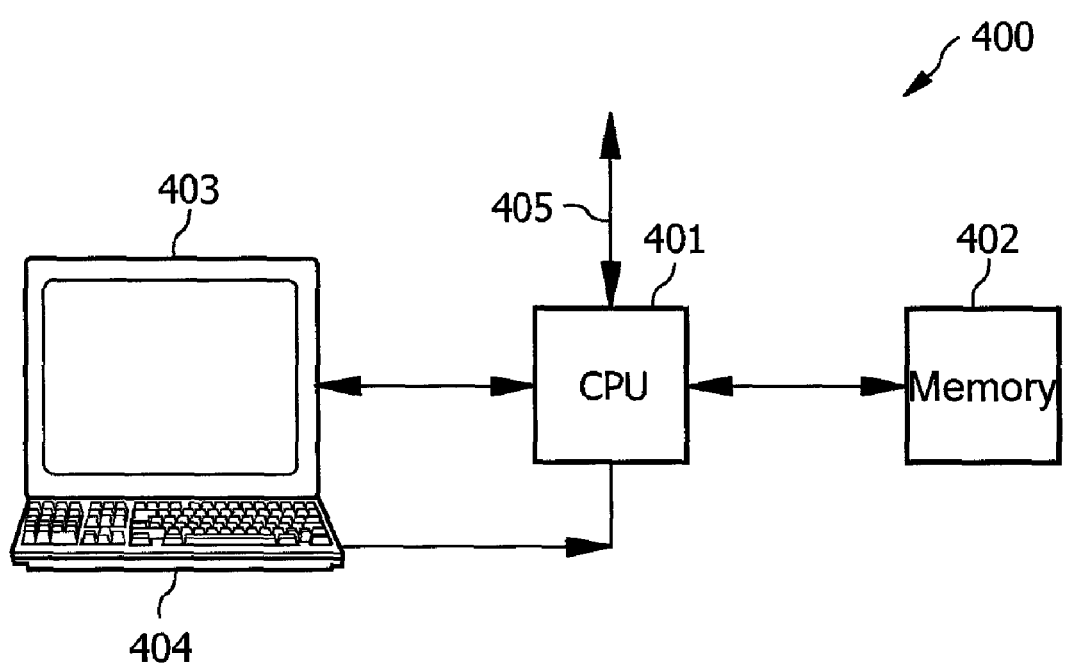
FIG. 3 shows an exemplary embodiment of an image processing device according to the present invention, for executing an exemplary embodiment of a method in accordance with the present invention.

FIG. 3 shows an exemplary embodiment of an image processing device according to the present invention for executing an exemplary embodiment of the method in accordance with the present invention. The image processing device 400 depicted in FIG. 3 comprises a central processing unit (CPU) or image processor 401 connected to a memory 402 for storing an image depicting an object of interest, such as a patient or a material to be analyzed. The data processor 401 may be connected to a plurality of input/output network or diagnosis devices, such as an MRI device. The data processor 401 may furthermore be connected to a display device 403, for example, a computer monitor, for displaying information or an image computed or adapted in the data processor 401. An operator or user may interact with the data processor 401 via a keyboard 404 and/or other output devices, which are not depicted in FIG. 3.

Furthermore, via the bus system 405, it may also be possible to connect the image processing and control processor 401 to, for example, a motion monitor, which monitors a motion of the object of interest. In case, for example, a lung of a patient is imaged, the motion sensor may be an exhalation sensor. In case, the heart is imaged, the motion sensor may be an electrocardiogram.

The examination of an object of interest according to the present invention may allow for a determination of a change in relaxation rate per injected amount of contrast agent on the basis of a series of measured relaxation rate values as a function of an overall application value.

Exemplary embodiments of the invention may be sold as a software option to MR scanner console workstations, CT scanner console workstations, or PET scanner console workstations, or SPECT scanner console workstations.

The invention claimed is:

1. An examination apparatus for examination of an object of interest, the examination apparatus comprising:
an acquisition unit configured to determine a first contrast agent concentration after a first contrast agent application and before a second contrast agent application and to determine a second contrast agent concentration after the second contrast agent application, resulting in a series of determined contrast agent concentration values as a function of an overall contrast agent application value, wherein application of the contrast agent is absent between the first contrast agent application and the second contrast agent application; and
a determination unit configured for:
fitting a linear slope to the series of determined contrast agent concentration values as the function of the overall contrast agent application value;
monitoring deviations of a linearity of the slope; and
determining a leakiness of the object of interest based on the monitored deviations;
wherein the fitting is performed based on a weighting of the first determined contrast agent concentration with a corresponding first error bar and a weighting of the second determined contrast agent concentration with a corresponding second error bar; and
wherein the examination apparatus is a magnetic resonance examination apparatus.

2. The examination apparatus of claim 1, further comprising:
a contrast agent application unit configured to perform the first contrast agent application at a first predetermined time and for performing the second contrast agent application at a second predetermined time.

3. The examination apparatus of claim 1,
wherein the first contrast agent concentration is determined based on a first relaxation rate and wherein the second contrast agent concentration is determined based on a second relaxation rate, wherein the series of determined contrast agent concentration values as the function of the overall contrast agent application value is a series of determined relaxation rate values as the function of the overall contrast agent application value.

4. The examination apparatus of claim 3, wherein the determination unit is further
configured to determine a change in relaxation rate per injected amount of contrast agent based on the series of the determined relaxation rate values.

5. The examination apparatus of claim 3,
wherein the first relaxation rate is based on a spin-spin transverse relaxation rate and incorporates magnetic field inhomogeneities.

6. The examination apparatus of claim 1,
wherein the determination of the leakiness is performed based on a fit of a non-linear model to the series of determined contrast agent concentration values.

7. The examination apparatus of claim 1,
wherein the object of interest comprises a first voxel and a second voxel;
wherein the monitoring of deviations of the linearity of the slope is performed for the first voxel and the second voxel, resulting in a discrimination of different areas within the object of interest.

8. The examination apparatus of claim 1, configured as one of the group consisting of a baggage inspection apparatus, a medical application apparatus, a material testing apparatus and a material science analysis apparatus.

9. The examination apparatus of claim 1, wherein a first application rate of the first contrast agent application is higher than a second application rate of the second contrast agent application.

10. A tangible computer readable medium embodying non-transitory computer instructions which, when being executed by a processor of an examination apparatus, is adapted to carry out the acts of:
performing a first contrast agent application;
performing a second contrast agent application; and
measuring a first contrast agent concentration after the first contrast agent application and before the second contrast agent application and measuring a second contrast agent concentration after the second contrast agent application, resulting in a series of measured contrast agent concentration values as a function of an overall contrast agent application value, wherein application of the contrast agent is absent between the first contrast agent application and the second contrast agent application; and
fitting a linear slope to the series of determined contrast agent concentration values as the function of the overall contrast agent application value;
monitoring deviations of the linearity of the slope; and
determining a leakiness of a tumor on the basis of the monitored deviations,
wherein the fitting is performed on the basis of a weighting of the first measured contrast agent concentration with a corresponding first error bar and a weighting of the second measured contrast agent concentration with a corresponding second error bar; and
wherein the examination apparatus is a magnetic resonance examination apparatus.

11. A method of examination of an object of interest using an examination apparatus, the method comprising the acts of:
performing a first contrast agent application;
performing a second contrast agent application;
determining a first contrast agent concentration after the first contrast agent application and before the second contrast agent application;
determining a second contrast agent concentration after the second contrast agent application, resulting in a series of determined contrast agent concentration values as a function of an overall contrast agent application value, wherein application of the contrast agent is absent between the first contrast agent application and the second contrast agent application; and
fitting a linear slope to the series of determined contrast agent concentration values as the function of the overall contrast agent application value;
monitoring deviations of the linearity of the slope; and
determining a leakiness of a tumor on the basis of the monitored deviations,
wherein the fitting is performed on the basis of a weighting of the first determined contrast agent concentration with a corresponding first error bar and a weighting of the second determined contrast agent concentration with a corresponding second error bar; and
wherein the examination apparatus is a magnetic resonance examination apparatus.

12. The method of claim 11,
wherein the first contrast agent concentration is determined on the basis of a first relaxation rate and wherein the second contrast agent concentration is determined on the basis of a second relaxation rate, wherein the series of determined contrast agent concentration values as the function of the overall contrast agent application value is a series of determined relaxation rate values as the function of the overall contrast agent application value.

13. The method of claim 12,
wherein the first relaxation rate is based on a spin-spin transverse relaxation rate and incorporates magnetic field in homogeneities.

14. The method of claim 12, further comprising the act of:
determining a change in relaxation rate per injected amount of contrast agent on the basis of the series of measured relaxation rate values.

* * * * *